(12) United States Patent
Zhu et al.

(10) Patent No.: US 10,674,994 B2
(45) Date of Patent: Jun. 9, 2020

(54) ULTRASONIC IMAGING DEVICE AND IMAGE PROCESSING METHOD

(71) Applicant: Hitachi, Ltd., Tokyo (JP)

(72) Inventors: Peifei Zhu, Tokyo (JP); Zisheng Li, Tokyo (JP); Yasuki Kakishita, Tokyo (JP); Mayumi Suzuki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 128 days.

(21) Appl. No.: 15/771,156

(22) PCT Filed: Nov. 24, 2016

(86) PCT No.: PCT/JP2016/084742
§ 371 (c)(1),
(2) Date: Apr. 26, 2018

(87) PCT Pub. No.: WO2017/094577
PCT Pub. Date: Jun. 8, 2017

(65) Prior Publication Data
US 2018/0325488 A1 Nov. 15, 2018

(30) Foreign Application Priority Data
Dec. 2, 2015 (JP) ................. 2015-235805

(51) Int. Cl.
*A61B 8/08* (2006.01)
*A61B 6/00* (2006.01)

(52) U.S. Cl.
CPC ............... *A61B 8/08* (2013.01); *A61B 6/463* (2013.01); *A61B 6/466* (2013.01); *A61B 6/5217* (2013.01);
(Continued)

(58) Field of Classification Search
CPC ....... A61B 6/463; A61B 6/466; A61B 6/5217; A61B 8/08; A61B 8/0883; A61B 8/483; A61B 8/523; G06T 2207/30048
See application file for complete search history.

(56) References Cited

U.S. PATENT DOCUMENTS

2010/0125203 A1 5/2010 Lee et al.
2011/0313291 A1 12/2011 Chono
(Continued)

FOREIGN PATENT DOCUMENTS

JP 2009-153600 A 7/2009
JP 2010-119847 A 6/2010
(Continued)

OTHER PUBLICATIONS

International Search Report of PCT/JP2016/084742 dated Feb. 14, 2017.

*Primary Examiner* — Nirav G Patel
(74) *Attorney, Agent, or Firm* — Mattingly & Malur, PC

(57) ABSTRACT

A standard view which satisfies recommendations defined in a guideline on acquisition of standard views is extracted at a time of using information about defined landmarks and a defined landmark geometry in the three-dimensional information. When 3D volume data on a subject is input (S301), an image processing apparatus extracts a landmark geometry including landmarks contained in the 3D volume data on the basis of a position relationship among the landmarks (S302), determines a standard view of the 3D volume data using the landmark geometry and a position relationship that satisfies recommendations in a guideline on the acquisition of the standard views (S303), and outputs the obtained standard view (S304) to display the standard view on a display.

13 Claims, 11 Drawing Sheets

(52) U.S. Cl.
CPC ............ *A61B 8/0883* (2013.01); *A61B 8/483* (2013.01); *A61B 8/523* (2013.01); *G06T 2207/30048* (2013.01)

(56) References Cited

U.S. PATENT DOCUMENTS

2014/0219524 A1    8/2014    Takeguchi et al.
2019/0125303 A1*  5/2019    Gronseth ............ A61B 8/4263

FOREIGN PATENT DOCUMENTS

WO        2010/092918 A1    8/2010
WO        2012/153539 A1    11/2012

* cited by examiner

FIG.7
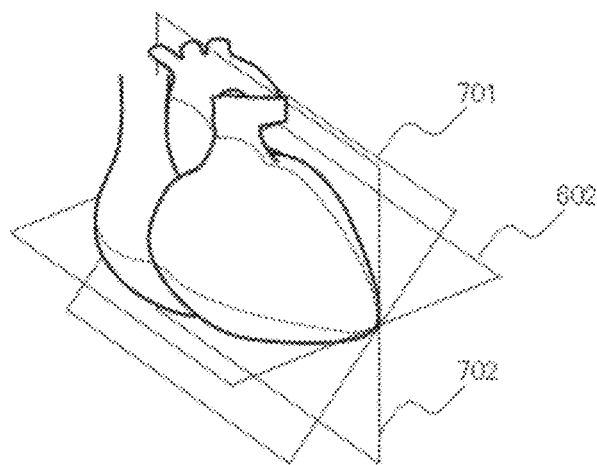
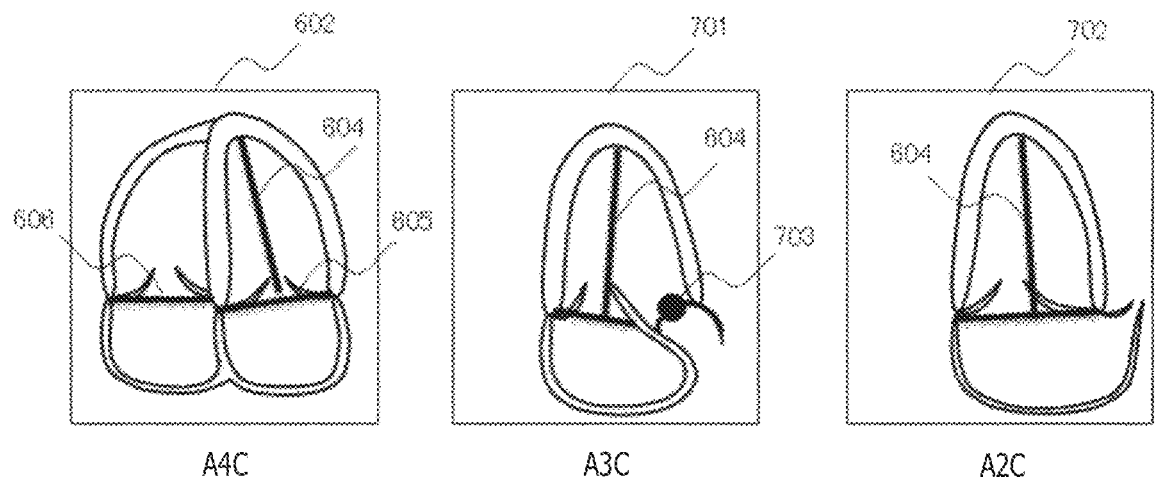
A4C  A3C  A2C (PCA) GEOMETRY x:

$x = \bar{x} + a_1 v_1 + a_2 v_2 + \cdots + a_n v_n,$
$a_1, a_2, \cdots, a_n$: WEIGHT OF PRINCIPAL COMPONENTS

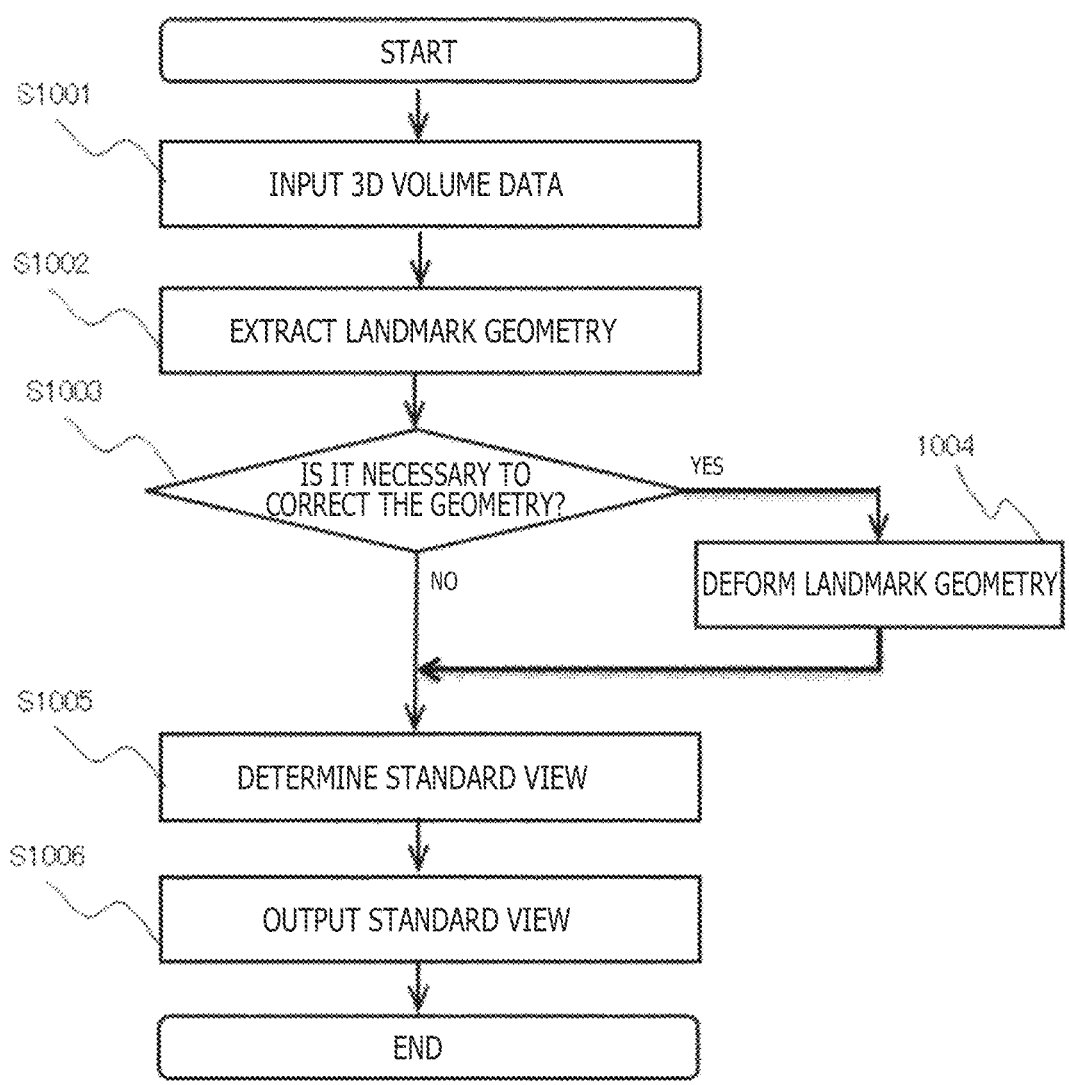

ULTRASONIC IMAGING DEVICE AND IMAGE PROCESSING METHOD

TECHNICAL FIELD

The present invention relates to a diagnostic ultrasound technique for extracting standard view information for diagnosis from three-dimensional information and providing the standard view information.

BACKGROUND ART

An ultrasound system such as a diagnostic ultrasound apparatus has characteristics capable of observing an interior of an object to be examined without destroying the object. The ultrasound system can be widely used particularly in a medical field as means capable of safe observation of internal tissues without the need of a surgical procedure such as laparotomy on a human body.

A heart is one of objects to be observed by the ultrasound system. A guideline is defined, for views of the heart that is the object to be examined, on the acquisition of several standard views (hereinafter, referred to as "guideline") so that a uniform consideration can be given no matter who observes the heart, and the ultrasound system provides images of the standard views based on this guideline. The standard views of the heart based on the guideline include parasternal views, apical views, subcostal views, suprasternal views, and the like.

A conventionally used method is one for imaging cardiac views one by one by an examiner who is a user while the examiner is operating an ultrasound probe. There has been recently proposed a system for acquiring 3D volume data that is three-dimensional information such as 3D cardiac ultrasound images using a special ultrasound probe, and automatically acquiring a plurality of standard views from the 3D volume data.

Examples of related prior art documents include Patent Document 1. A technique of Patent Document 1 intends to achieve improvement of boundary detection of a heart, and includes deforming a boundary model so that an error between a boundary pattern obtained by applying the boundary model to volume data and a predetermined boundary pattern model becomes small. Next, a boundary detecting unit, which is configured to detect a left ventricle boundary from the volume data, displays the detected left ventricle boundary on an image of a cardiac view orthogonal to at least one axis of three axes of a left ventricle coordinate system together with the image of the cardiac view.

PRIOR ART DOCUMENT

Patent Document

Patent Document 1: WO12/153539

SUMMARY OF THE INVENTION

Problem to be Solved by the Invention

Although Patent Document 1 enables the detection of the boundary of the heart and the display of the boundary on the image of the cardiac view orthogonal to one axis of the coordinate system, Patent Document 1 does not describe a method for identifying a standard view of the heart from the detected boundary. Furthermore, in Patent Document 1, a boundary line is optimized using all feature points present on the boundary when the boundary model is used; thus, it is considered that extensive calculations are necessary and that the boundary is difficult to detect at high speed.

An object of the present invention is to provide an ultrasonic imaging device and an image processing method that can solve the problems described above and that can extract a standard view that satisfy recommendations in a guideline for three-dimensional images of an object to be observed with high accuracy.

Means for Solving the Problem

To attain the object, the present invention provides an ultrasonic imaging device including an image processing apparatus. The image processing apparatus extracts a landmark geometry that contains landmarks in three-dimensional information about a subject obtained by transmitting and receiving ultrasound waves, and determines a standard view based on the three-dimensional information using the landmark geometry and a position relationship that satisfies recommendations in a guideline.

Furthermore, to attain the object, the present invention provides an image processing method executed by an image processing apparatus, including: extracting a landmark geometry that contains landmarks in three-dimensional information about a subject; and determining a standard view based on the three-dimensional information using the landmark geometry and a position relationship that satisfies recommendations in a guideline.

Effect of the Invention

According to the present invention, an ultrasonic imaging device for acquiring a cardiac standard view from three-dimensional information can acquire a robust and high-accuracy standard view from an extracted landmark geometry on the basis of recommendations in a guideline.

BRIEF DESCRIPTION OF THE DRAWINGS

FIG. 7 shows an example of extracting three standard long-axis views according to the first embodiment.

FIG. 10 shows an example of an overall flow of standard view extraction according to the second embodiment.

MODES FOR CARRYING OUT THE INVENTION

Figure 1:
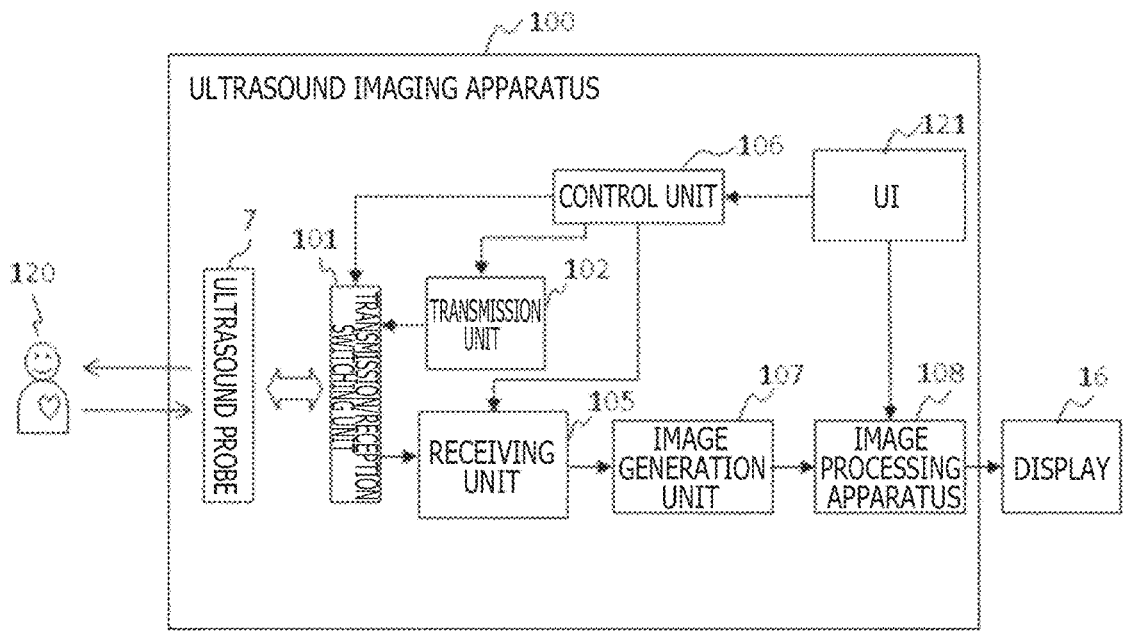
FIG. 1 is a block diagram showing an example of an overall configuration of an ultrasonic imaging device according to a first embodiment.

Embodiments of the present invention will be described hereinafter with reference to the drawings. It is noted that the same parts are denoted by the same reference characters in all drawings in principle for describing the embodiments, and that repetitive description thereof will be omitted. In the present specification, a landmark means a site that is artificially set since being regarded as being anatomically significant in an organ such as a heart. In the following embodiments, a case of acquiring an apical 4-chamber (A4C) view will be mainly described to satisfy recommendations in a guideline on the acquisition of standard views of a heart. The present invention is also applicable to standard views including an apical 2-chamber (A2C) view, a left parasternal long-axis (A3C: Apical 3-Chamber) view, and a left parasternal short-axis (PSX) view. Recommendations during observation are also defined for these standard views in the guideline, and mutual position relationships and the like among these standard views will be sequentially described in the description of the following embodiments.

First Embodiment

A first embodiment is an embodiment of an ultrasonic imaging device provided with an image processing apparatus. The image processing apparatus is configured to extract a landmark geometry including landmarks in three-dimensional information about a subject obtained by transmitting and receiving ultrasound waves, and to determine a standard view based on the three-dimensional information using the landmark geometry and a position relationship that satisfies the recommendations in the guideline. The first embodiment is also an embodiment of an image processing method by the image processing apparatus, the method including: extracting, by the image processing apparatus, a landmark geometry including landmarks in three-dimensional information about a subject, and determining, by the image processing apparatus, a standard view based on the three-dimensional information using the landmark geometry and a position relationship that satisfies the recommendations in the guideline on the acquisition of standard views.

The ultrasonic imaging device in the first embodiment is configured with, for example, an ultrasound probe 7, an image generation unit 107, and an image processing apparatus 108, as shown in FIG. 1. The ultrasound probe 7 transmits an ultrasound wave to a subject 120 via a transmission/reception switching unit 101 and receives an ultrasonic wave from the subject 120. The image generation unit 107 generates an ultrasound image from a signal received by the ultrasound probe 7. The image processing apparatus 108 receives ultrasound 3D volume data from the image generation unit 107 as three-dimensional information and processes the three-dimensional information. It is noted that a hardware configuration of the ultrasonic imaging device shown in FIG. 1 is commonly used in other embodiments.

<Configuration and Operation>

A specific configuration of the ultrasonic imaging device in the present embodiment will be further described. As shown in FIG. 1, the ultrasonic imaging device in the present embodiment is further configured with a transmission unit 102, the transmission/reception switching unit 101, a receiving unit 105, a user interface (UI) 121, and a control unit 106 as well as the ultrasound probe 7, the image generation unit 107, and the image processing apparatus 108. Furthermore, a display 16 that serves as an image display unit is connected to the ultrasonic imaging device.

The transmission unit 102 generates a transmission signal under control of the control unit 106 and delivers the transmission signal to each of a plurality of ultrasound elements that constitute the ultrasound probe 7. The plurality of ultrasound elements of the ultrasound probe 7 thereby transmit ultrasound waves toward the subject 120. The ultrasound waves subjected to reflection or the like by the subject 120 arrive at and are received again by the plurality of ultrasound elements of the ultrasound probe 7, and the ultrasound waves are converted into electrical signals. The signals received by the ultrasound elements are each delayed by a predetermined delay amount in response to a reception focus position and then added up, that is, subjected to phasing addition by the receiving unit 105. This process is thereby repeated for each of a plurality of reception focuses. The receiving unit 105 delivers the signals after the phasing addition to the image generation unit 107. The transmission/reception switching unit 101 selectively connects the transmission unit 102 or the receiving unit 105 to the ultrasound probe 7.

The image generation unit 107 performs a process, for example, for arranging the phasing-added signals received from the receiving unit 105 at positions corresponding to the reception focuses, and generates an ultrasound image as the 3D volume data. The image processing apparatus 108 receives the 3D volume data from the image generation unit 107 and extracts a standard view. In the configuration of FIG. 1, the display 16 that serves as the image display unit is installed outside of the ultrasonic imaging device; alternatively, the display 16 may be configured to be installed as part of the user interface 121 of the ultrasonic imaging device 100 as shown in FIG. 2 to be described below.

Configurations and operations of the image processing apparatus 108 and the user interface 121 will be described in detail below with reference to FIG. 2. FIG. 2 is a block diagram showing a hardware configuration of the image processing apparatus 108 and the user interface 121. Like FIG. 1, the hardware configuration shown in FIG. 2 is commonly used in the other embodiments to be described later.

Figure 2:
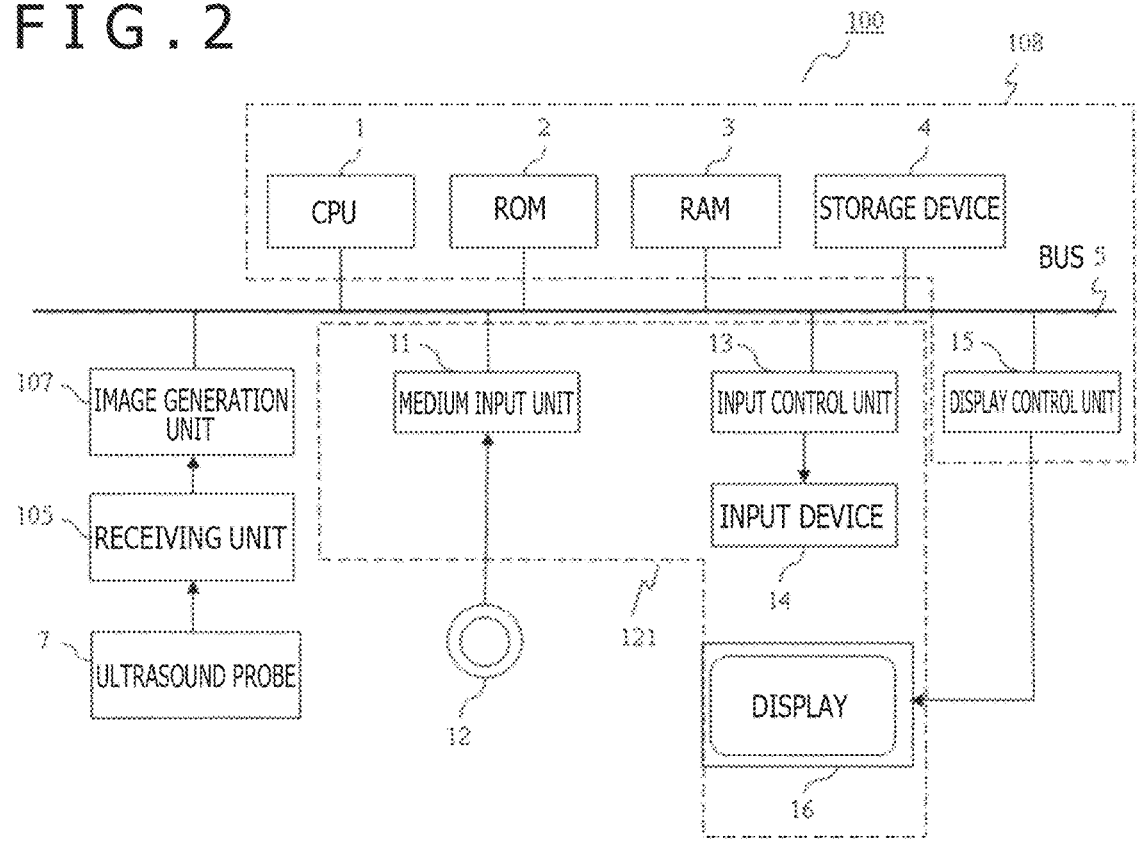
FIG. 2 is a block diagram showing an example of a hardware configuration of the ultrasonic imaging device according to the first embodiment.

As obvious from FIG. 2, the image processing apparatus 108 is configured with a central processing unit (CPU) 1, a nonvolatile memory (ROM) 2, a volatile memory (RAM) 3, a storage device 4, and a display control unit 15. The user interface 121 is configured with a medium input unit 11, an input control unit 13, an input device 14, and the display 16. The medium input unit 11, the input control unit 13, the display control unit 15, and the image generation unit 107 are connected to one another by a data bus 5 of the image processing apparatus 108. Furthermore, the display control unit 15 is connected to the display 16, and exercises display control over the display 16, for example, exercises control such that image data obtained by a process performed by the CPU 1 is displayed on the display 16.

A program and various data for a computing process necessary for realizing the operation of the image processing apparatus 108 and performed by the CPU 1 are stored in at least one of the ROM 2 and the RAM 3 in advance. Various processes of the image processing apparatus 108 are realized by the CPU 1 executing the program stored in at least one of the ROM 2 and the RAM 3 in advance. It is noted that the program executed by the CPU 1 may be stored in, for example, a storage medium 12 such as an optical disk and that the medium input unit 11 such as an optical disk drive may read the program and store the program in the RAM 3.

Alternatively, the program may be stored in the storage device 4 and loaded into the RAM 3 from the storage device 4. In another alternative, the program may be stored in the ROM 2 in advance. Furthermore, the storage device 4 includes a geometric model database that is not shown. This geometric model database contains, as information about a landmark geometry to be described later, an average geometry of landmarks of an object to be examined such as a heart of the subject, geometric parameters of principal components, and the like. Appropriately adjusting the information about the landmark geometry within this database makes it possible to deform the landmark geometry, and deformation is used to correct the landmark geometry to be described later.

The input device 14 of the user interface 12 is a device that receives user's operation and includes, for example, a keyboard, a track ball, an operation panel, and a foot switch. The input control unit 13 receives an operation instruction input from the input device 14 by a user. The operation instruction received by the input control unit 13 is executed and processed by the CPU 1.

Figure 3:
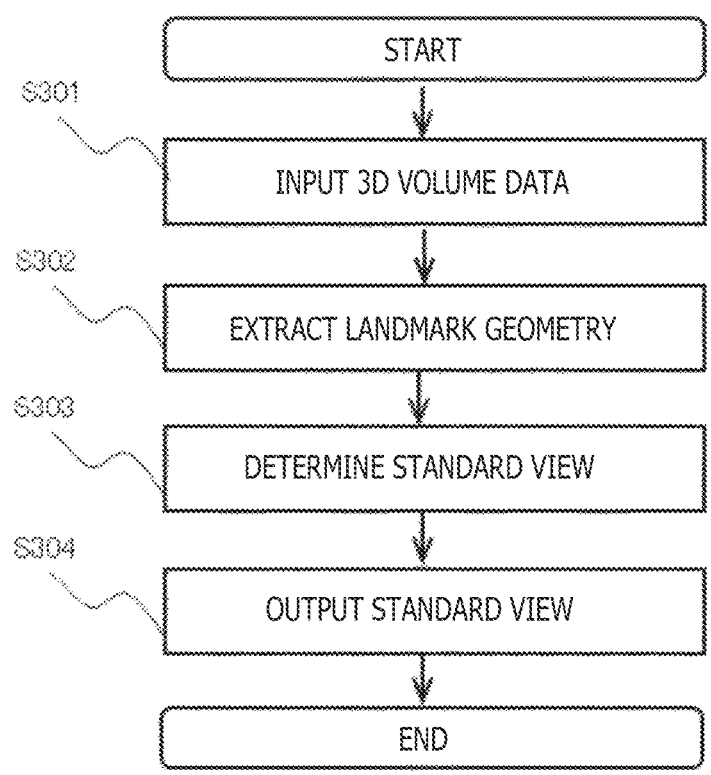
FIG. 3 shows an example of an overall flow of standard view extraction according to the first embodiment.

Processes performed by the image processing apparatus 108 in the present embodiment will next be described using an overall flowchart of standard view extraction shown in FIG. 3. The processes in this flowchart can be realized by execution of the program by the CPU 1 described above.

First, in Step 301, (hereinafter, indicated by "S301"), generated ultrasound 3D volume data is input to the image processing apparatus 108 from the image generation unit 107.

In S302, the image processing apparatus 108 extracts a landmark geometry by a method based on, for example, a geometric model. The geometric model is a set of vertexes that constitute a contour of a cardiac muscle of a heart present on a medical image or a set of set landmarks. Types of geometric model include a patch model for describing what each patch of the image looks like around each landmark and a shape model for describing a shape variation, as will be described later with reference to FIG. 5. The geometric model database in the storage device 4 stores a constructed patch model and a constructed shape model in advance. The image processing apparatus 108 reads these models and calculates initial coordinates of positions of landmarks and response images of local regions using the patch model for the input unknown 3D volume data. The local region means a given region around each landmark. Furthermore, the image processing apparatus 108 optimizes positions of feature points such as the vertexes under constraints of the shape model. The image processing apparatus 108 can extract the geometry by repeating the process until all the feature points arrive at stable positions.

In S303, the image processing apparatus 108 calculates a magnitude of each of observation sites and a length between the observation sites from the geometry extracted in S302 of extracting the landmark geometry, and extracts a view that satisfies the recommendations in the guideline on the acquisition of standard views. The recommendations in this guideline for, for example, the A4C are that a view captures a position at which an annulus diameter of a mitral valve becomes a maximum, a position at which an annulus diameter of a tricuspid valve becomes a maximum, a position at which a ventricular length becomes a maximum, and/or the like. The recommendations during observation of the A3C, the A2C, and the like that are other standard views are also defined in the guideline, and views that satisfy the recommendations in the guideline are extracted.

In S304, the CPU 1 of the image processing apparatus 108 outputs the standard view determined in S303 of determining the standard view, and the display control unit 15 transmits the standard view to the display 16 on which an image of the standard view is displayed.

Figure 4:
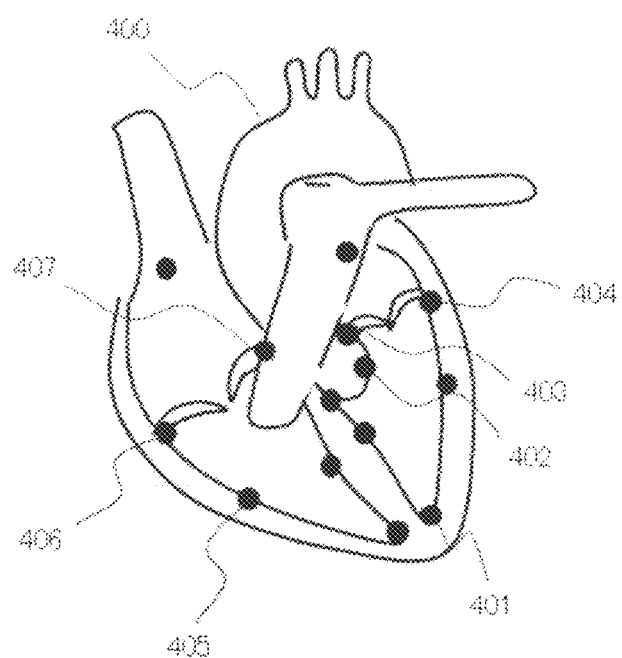
FIG. 4 shows an example of setting landmarks of a heart according to the first embodiment.

Step 302 of extracting the landmark geometry in the present embodiment will next be described in detail. FIG. 4 shows an example of setting landmarks of the heart. As indicated by black circles in FIG. 4, positions with abundant feature information including an apex cordis 401 that is an apical end portion of a heart 400, an aortic valve 402 that is a valve between a left ventricle and an aorta, a septum 403 of the mitral valve that is a valve between the left ventricle and a left atrium, a side wall 404 of the mitral valve, a central side wall 405 of a right ventricle, a side wall 406 of the tricuspid valve that is a valve between the right ventricle and the right atrium, a septum 407 of the tricuspid valve, and the like are set to the landmarks. The landmarks also include positions necessary for extracting the standard view. For example, the landmarks include the septum 403 of the mitral valve and the side wall 404 of the mitral valve that are two endpoints of a maximum annulus diameter of the mitral valve for capturing the position at which the annulus diameter becomes a maximum.

As a method of extracting the landmark geometry, a method based on, for example, a constrained local model (CLM) is used. As described above, the geometric model is, for example, a set of vertexes that constitute a contour of a cardiac muscle of the heart present on a medical image or a set of the landmarks shown in FIG. 4. The CLM is configured with two phases, i.e., construction of the geometric model and extraction thereof. First, in the geometric model construction phase, learning of what part corresponds to each landmark of the heart is carried out. Information about the learned landmark geometry is stored in the storage device 4. In the subsequent geometry extraction phase, landmarks of the heart are searched from within the image using the data learned in the geometric model construction and stored.

Figure 5:
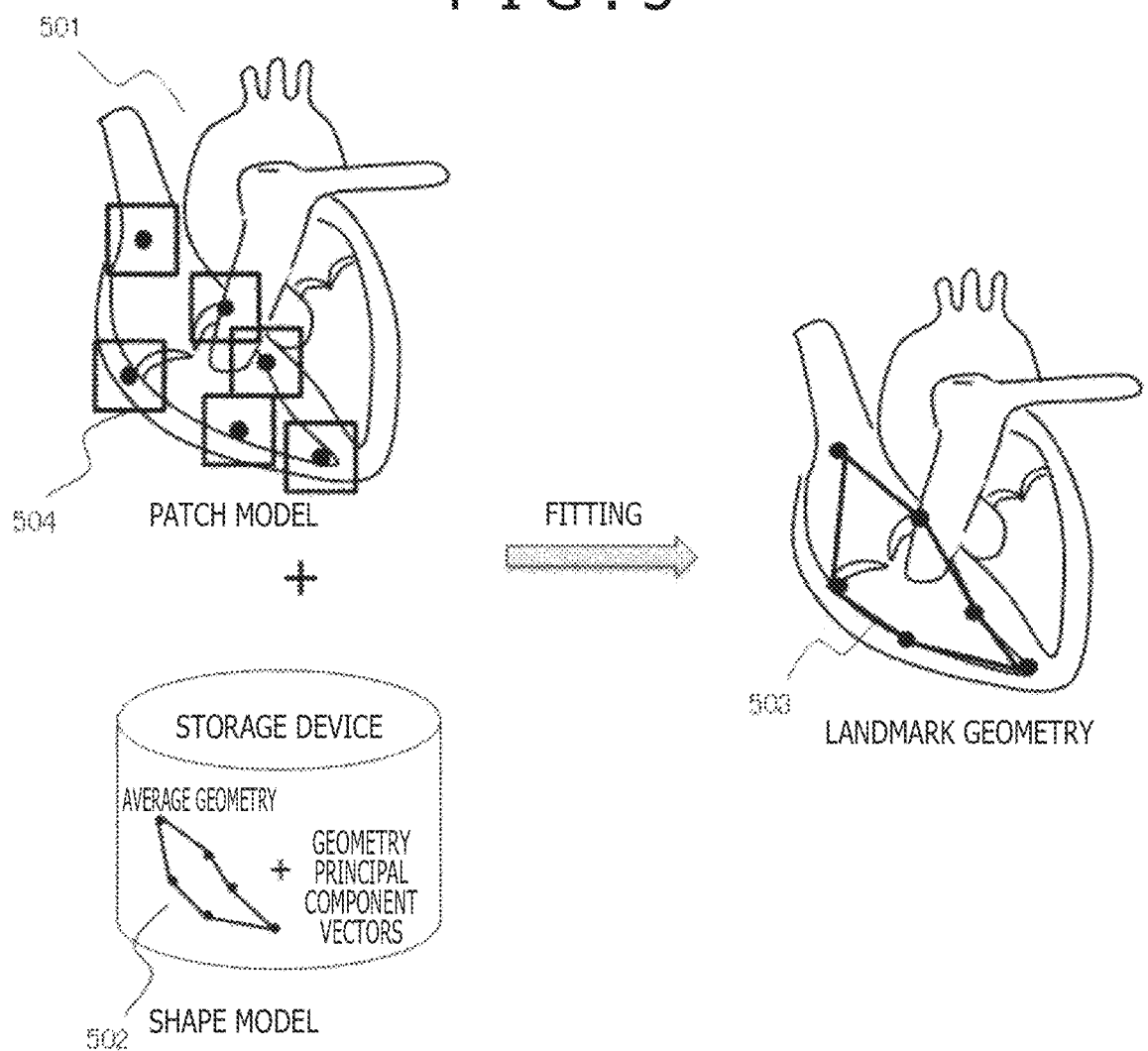
FIG. 5 shows an example of construction and extraction of a landmark geometry according to the first embodiment.

FIG. 5 schematically shows an example of the construction and extraction of the model of the landmark geometry according to the present embodiment. When the CLM method, for example, is used, the model is configured with two parts. One of the two parts is a patch model 501 for describing what each patch of the image looks like around each feature point, and the other part is a shape model 502 for describing a shape variation.

The patch model 501 is constructed using a method based on, for example, Hough Forest, which is support vector machine (SVM). When Hough Forest is used, then a decision tree for executing detailed determination related to directions of and distances among various landmarks present in the volume data is prepared, and a plurality of decision trees are combined, thereby making it possible to generate a feature classifier capable of similarly obtaining directions of and distances among arbitrary feature points for unknown volume data. It is thereby possible to acquire, from the unknown 3D volume data, bounding boxes 504 each around a site of interest input as a feature point and response images of local regions.

The shape model is constructed using, for example, principal component analysis (PCA). The shape model contains an average geometry and geometry principal component vectors that indicate a type of change. The average geometry is obtained by calculating an average of all geometries and can be regarded as a characteristic common to all hearts. The type of change is obtained by subtracting the average geometry from each geometry and represents how the geometry changes from the average geometry. Owing to this, the landmark geometry is generated by using types of change as several bases and adding the average geometry to a combination of the geometry and values of these bases.

The landmark geometry is extracted from the patch model 501 and the shape model 502 thus constructed, as follows. The response image of each local region is acquired while estimating initial coordinates of the position of each landmark by the patch model 501. When a high value is obtained in the response image, it means that a matching score is high; otherwise, it means that a matching score is low. Next, a quadric is fit to the response image. The quadric is optimized under shape constrains, thereby obtaining a new feature point position. Repeating this process until all the points arrive at stable positions makes it possible to extract a landmark geometry 503.

It is noted that a well-known method such as an active shape model method or an active appearance model method is applicable to the extraction of the landmark geometry as an alternative to the CLM method described above.

Figure 6:
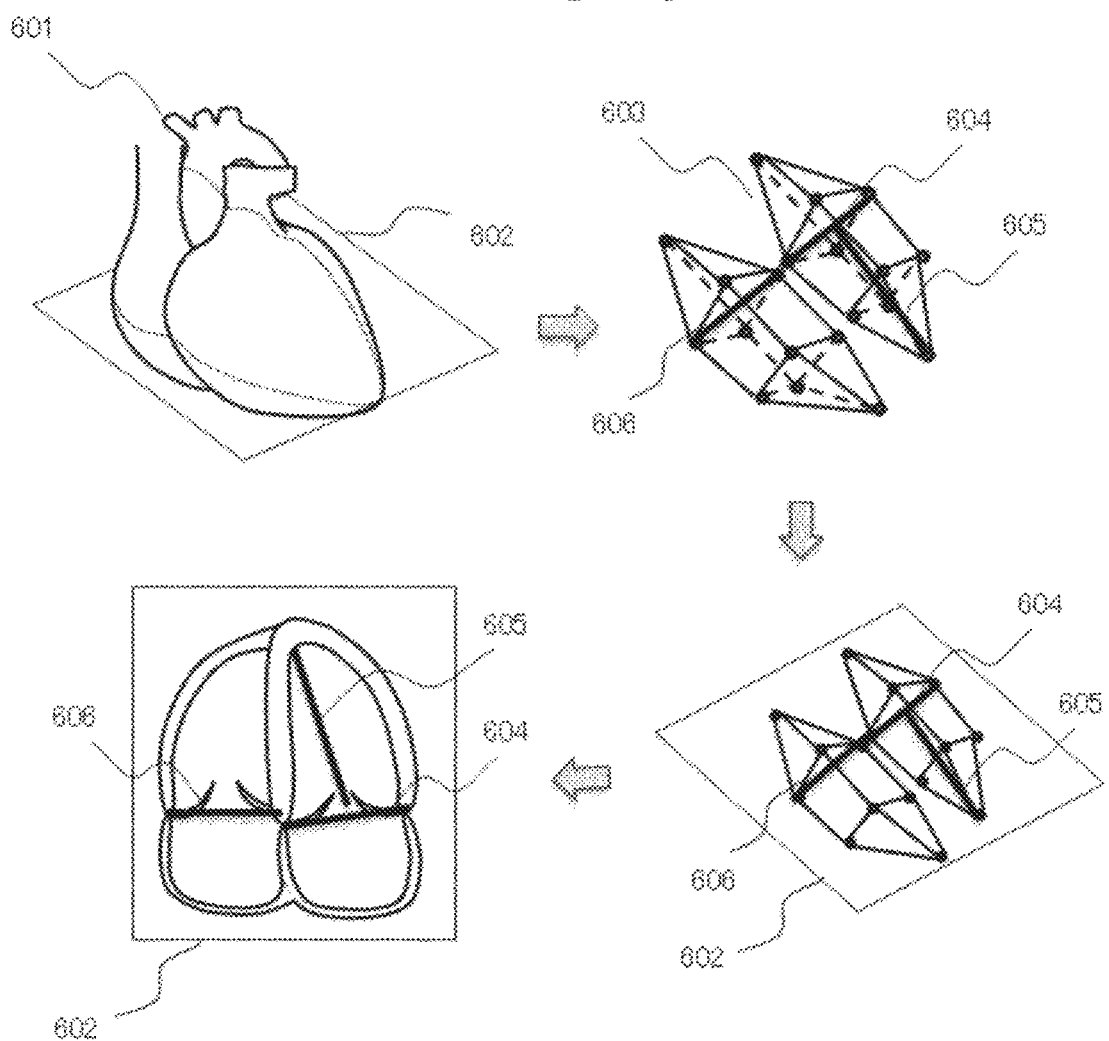
FIG. 6 shows an example of extracting a standard view A4C according to the first embodiment.

Next, the process in S303 of determining the standard view, in the flow of the standard view extraction in the present embodiment, for determining the standard view from the landmark geometry extracted in S302 of extracting the landmark geometry will be described with reference to FIG. 6. FIG. 6 shows an example of extracting the standard view A4C from a landmark geometry 601. An A4C 602 is a standard view that satisfies the recommendations defined in the guideline in which recommendations a standard view captures a position 604 at which the annulus diameter of the mitral valve becomes a maximum, a position 606 at which the annulus diameter of the tricuspid valve becomes a maximum, a position 605 at which the ventricular length becomes a maximum, and/or the like. It is noted that the position at which the ventricular length becomes a maximum is defined as a position at which a distance between an annulus center of the mitral valve and the apex cordis becomes a maximum.

In S303 of determining the standard view, the image processing apparatus 108 calculates for the geometry extracted in S302 the position 604 at which the annulus diameter of the mitral valve becomes a maximum, the position 606 at which the annulus diameter of the tricuspid valve becomes a maximum, and/or the position 605 at which the ventricular length becomes a maximum, as well as lengths thereof. These maximum diameter/length positions are positions pre-defined in the geometric model and are unnecessary to calculate anew. For example, to capture the position at which the annulus diameter of the mitral valve becomes a maximum, the septum 403 of the mitral valve and the side wall 404 of the mitral valve that are the two endpoints of the maximum diameter are set as the landmarks. This setting enables a septum of a mitral valve and a side wall of the mitral valve as landmarks obtained under constraints of the shape model to be set as the endpoints of a maximum diameter of the mitral valve when the landmark geometry is extracted from unknown volume data. To capture the position at which the annulus diameter of the tricuspid valve becomes a maximum and the position at which the ventricular length becomes a maximum, the landmarks may be set in advance. It is noted that the recommendations during observation of the A3C and A2C that are the other standard views are also defined in the guideline, and views that satisfy the recommendations can be, therefore, determined as standard views.

As described above, the A4C is the view that passes through the position 604 at which the annulus diameter of the mitral valve becomes a maximum, the position 606 at which the annulus diameter of the tricuspid valve becomes a maximum, and/or the position 605 at which the ventricular length becomes a maximum. It is noted, however, the image processing apparatus 108 in the present embodiment is configured to determine a view by the recommendations in the guideline kept in balance when there is no view that satisfies all the recommendations in the guideline. For example, the image processing apparatus 108 adds up three angles formed between a view and a direction in which the annulus diameter of the mitral valve becomes a maximum, between the view and a direction in which the annulus diameter of the tricuspid valve becomes a maximum, and between the view and a direction in which the ventricular length becomes maximum, to thereby minimize the obtained result. The image processing apparatus 108 determines the view with respect to which a sum of the three angles, that is, a sum of angles of the directions of a plurality of position relationships among the landmarks becomes a minimum as a standard view, i.e., the A4C view.

FIG. 7 schematically shows an example of extracting three standard long-axis views. The A4C view can be determined as already described with reference to FIG. 6. An A3C 701 is a view that passes through the position 604 at which the ventricular length becomes a maximum and the aortic valve 703. Specifically, the image processing apparatus 108 may extract a view which is obtained by rotating the A4C view about a ventricular long axis at the position 604 as a central axis and which passes through the aortic valve 703. On the other hand, an A2C 702 is a view which passes through the position 604 at which the ventricular length becomes a maximum and which is characterized in that an image of the view contains only the left ventricle and the left atrium. The image processing apparatus 108 may use an extraction method of the A2C view 702 to rotate the A4C view about the ventricular length long axis at the position 604 as the central axis and to extract a view the image of which contains only the left ventricle and the left atrium.

Figure 8:
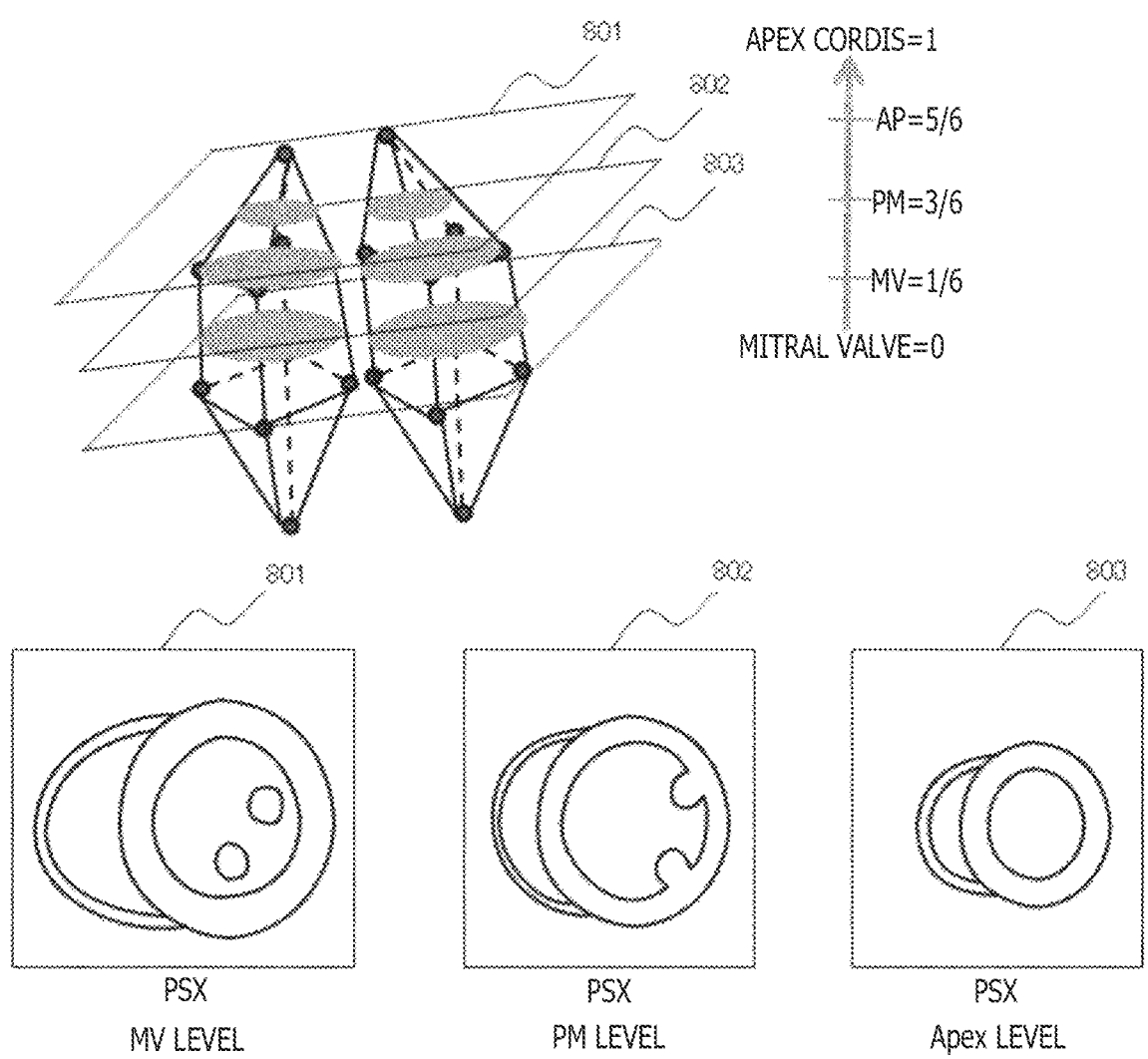
FIG. 8 shows an example of extracting three standard short-axis views according to the first embodiment.

FIG. 8 schematically shows an example of extracting three standard short-axis views. A landmark geometry shown in an upper part of FIG. 8 is the same as the landmark geometry obtained in S302 of extracting the landmark geometry as previously described. The three short-axis views are a PSX view at MV level 801, a PSX view at PM level 802, and a PSX view at Apex level 803. Left sternal short-axis views (PSX) are views parallel to a mitral valve annulus and classified into three levels depending on positions. A recommended view as the PSX view at the MV level is a view near the mitral valve, a recommended view as the PSX view at the PM level is a view near a connection section between a papillary muscle and a cardiac muscle, and a recommended view as the PSX view at the Apex level is a view near the apex cordis. Parallel translation amounts are extracted by specifying ratios in advance such as 1/6 for the MV level, 3/6 for the PM level, and 5/6 for the Apex level with, for example, a center of the mitral valve defined as 0 and an apex cordis center defined as 1. A mitral valve annulus view is a view which passes through the landmarks such as the septum 403 of the mitral valve and the side wall 404 of the mitral valve defined in the geometry model. The image processing apparatus 108 can extract the three short-axis views as the standard views by determining the mitral valve annulus view and the position of the connection section between the papillary muscle and the cardiac muscle.

The ultrasonic imaging device in the present embodiment described so far can extract the standard view compliant with recommended criteria in the guideline from the landmark geometry that is the three-dimensional information robustly and with high accuracy.

Second Embodiment

A second embodiment is an embodiment of the ultrasonic imaging device provided with the image processing apparatus, and the image processing apparatus is configured such that the user checks the extracted geometry on a screen, and the landmark geometry can be deformed by adjustment of geometric parameters if it is necessary to correct the geometry in the extraction of the landmark geometry by the image processing apparatus of the ultrasonic imaging device in the first embodiment.

Figure 9A:
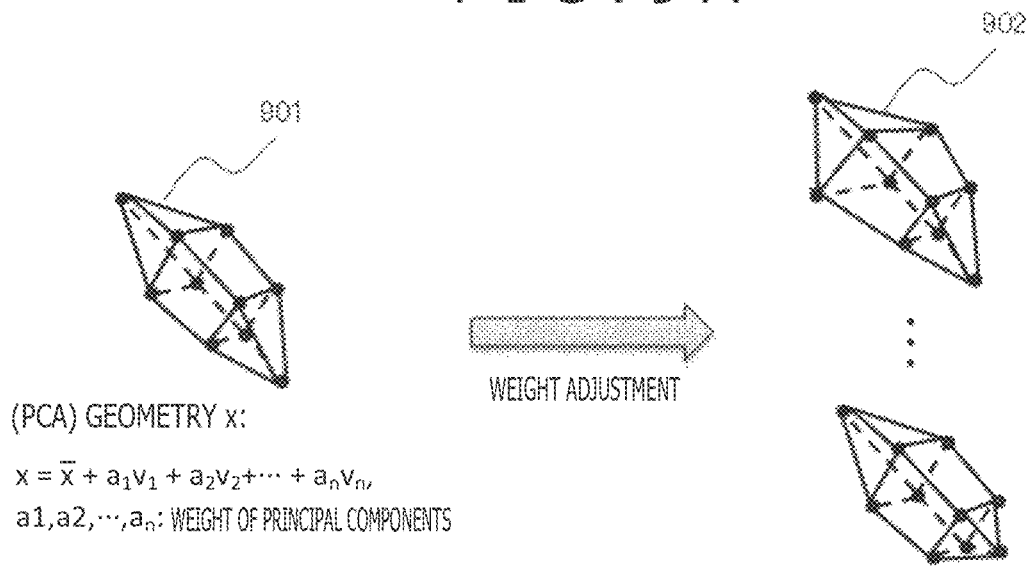
FIG. 9A shows an example of deforming a landmark geometry by geometric parameter adjustment according to a second embodiment.

FIG. 9A is a schematic diagram showing an example of deformation by adjustment of the geometric parameters in the second embodiment. A geometry 901 contains an average geometry and geometry principal component vectors that indicate a type of change, and is represented by, for example, a function of the following (Equation 1).

$$x = \bar{x} + a_1 v_1 + a_2 v_2 + \ldots + a_n v_n \quad \text{(Equation 1)}$$

In (Equation 1), $v_1, v_2, \ldots,$ and $v_n$ are principal component vectors of the geometry, and $a_1, a_2 \ldots$ and $a_n$ are weighting factors for the principal component vectors, respectively, that is, principal component parameters.

Adjusting values of the weighting factors that are the geometric parameters changes a state of a resultant deformed geometry 902. For example, if it is assumed that $v_1$ and $v_2$ are the principal component vectors related to a geometry of the mitral valve annulus, the mitral valve annulus can be subjected to scaling, rotation, and geometric deformation by adjusting the corresponding weighting factors $a_1$ and $a_2$. A relationship between geometries of landmarks significant for the extraction of a standard view, for example, geometries of the mitral valve annulus, a tricuspid valve annulus, and an apex cordis portion and the weighting factors that are the geometric parameters are analyzed, and values of these weighting factors are appropriately adjusted. It is thereby possible to extract an appropriate geometry of the object to be examined.

Figure 9B:
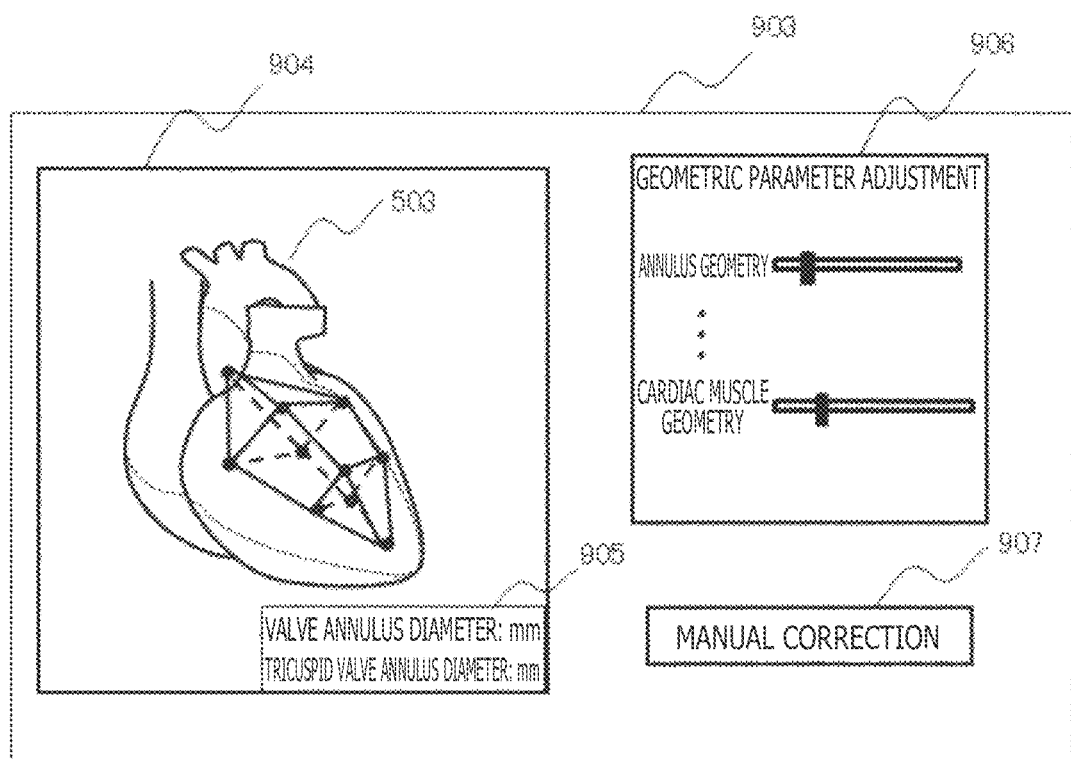
FIG. 9B shows an example of an interface for the geometric parameter adjustment according to the second embodiment.

FIG. 9B shows an example of an interface for geometric parameter adjustment displayed on the display that serves as the image display unit according to the present embodiment. An interface 903 is provided with a display region 904 in which the extracted landmark geometry is displayed, a measured numeric value display region 905, a control bar 906 for the geometric parameter adjustment, and a manual correction instruction button 907. In other words, the image processing apparatus 108 of the ultrasonic imaging device 100 in the present embodiment takes a standard view from the extracted landmark geometry 503, detects the magnitude of each observation site and the length between the observation sites from the extracted landmark geometry 503, and displays these measured numeric values in the measured value display region 905 on the screen of the interface 903.

The user checks the numeric values of the extracted geometry on the screen, and the landmark geometry is deformed by adjustment of the geometric parameters for valve annulus geometries, a cardiac muscle geometry, and the like if it is necessary to correct the geometry. In other words, by adjusting the control bar 906, the corresponding mitral valve annulus can be subjected to scaling, rotation, geometric deformation, and the like. Furthermore, the user can make a manual fine adjustment of the geometry if needed. Specifically, user's depressing the manual correction instruction button 907 turns a manual correction program stored in advance into a state of running on the CPU 1. In addition, it is possible to manually correct a position of a desired landmark in the landmark geometry 503 displayed in the display region 904 and an overall geometry in response to deformation of the desired landmark by user's drag-and-drop using a mouse or the like.

FIG. 10 shows an example of an overall flow of standard view extraction according to the second embodiment. In S1001 to S1002 of FIG. 10, the image processing apparatus 108 extracts a defined landmark geometry similarly to the processing flow shown in FIG. 3 according to the first embodiment. In S1003, the user checks the landmark geometry 503 displayed on the screen of the interface 903, and the image processing apparatus 108 determines whether it is necessary to correct the geometry. When it is necessary to correct the geometry (YES), the image processing apparatus 108 adjusts the geometric parameters using the control bar 906 or the like of the interface 903 shown in FIG. 9B. The image processing apparatus 108 thereby executes deformation of the landmark geometry in S1004, and can extract an appropriate landmark geometry of the object to be examined. On the other hand, when it is determined that it is unnecessary to correct the geometry (NO), the flow goes to S1005 of determining a standard view. The image processing apparatus 108 determines a standard view on the basis of the geometry corrected or determined to be unnecessary to correct in S1005, and outputs the standard view in S1006 to transmit the standard view to the display 16, so that an image of the standard view can be displayed.

According to the present embodiment, the user checks the extracted geometry on the screen, and the landmark geometry can be deformed by adjustment of the geometric parameters if it is necessary to correct the geometry; thus, it is possible to extract the more accurate landmark geometry and display the image of the standard view.

Third Embodiment

A third embodiment is an embodiment of the ultrasonic imaging device provided with the image processing apparatus, and the image processing apparatus is configured such that a deviation between a geometry of a local site and an average geometry is calculated when the local site is unclear, and the local site can be removed as an abnormal site when the deviation is out of an allowable range in the extraction of the landmark geometry by the image processing apparatus of the ultrasonic imaging device. In other words, the second embodiment is the embodiment of the ultrasonic imaging device, in which the image processing apparatus is configured to determine the extracted landmark geometry as a first landmark geometry, calculate the deviation between the first landmark geometry and the average geometry of the landmarks stored in the storage device, delete from the first landmark geometry a local geometry, the deviation on which in the first landmark geometry is equal to or higher than a predetermined value, extract a second landmark geometry containing landmark geometries other than the local geometry, and determine a standard view using the extracted second landmark geometry.

Figure 11:
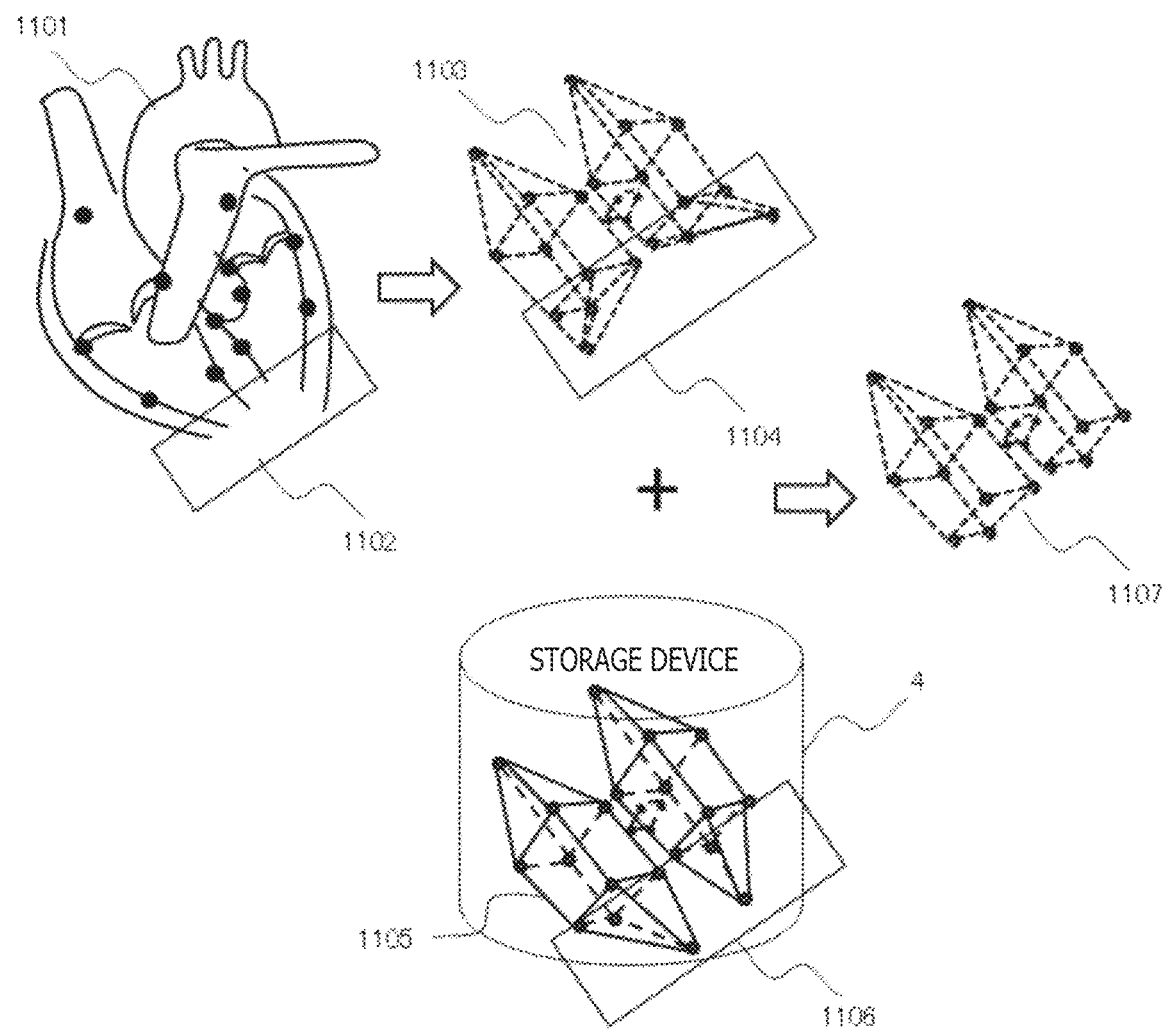
FIG. 11 shows an example of removing an abnormal site from a landmark geometry according to a third embodiment.

FIG. 11 is a schematic diagram showing an example of removing the abnormal site from the first landmark geometry. If a local image 1102 of a local site in an apex cordis portion of the left ventricle and the right ventricle is unclear for 3D volume data 1101, it is difficult to detect feature points in the apex cordis portion because of lack of an image feature amount near the apex cordis portion. Owing to this, an apex cordis portion dispersion 1104 is generated in the extracted first landmark geometry 1103, resulting in an influence on accuracy for subsequent determination of a standard view. To address the problem, the image processing apparatus 108 calculates a deviation between the extracted landmark geometry 1103 and an average geometry 1105 stored in the storage device 4 in advance and read by the CPU 1, removes the local site as the abnormal site when the deviation on the local site, for example, deviation between the extracted apex cordis portion 1104 and an apex cordis portion 1106 in the average geometry is out of an allowable range, and stores only a second landmark geometry 1107 in a range in which the landmark geometry is determined as a normal geometry. Like the second embodiment, the image processing apparatus 108 can be configured such that the user can manually perform correction and removal related to the abnormal site.

Figure 12:
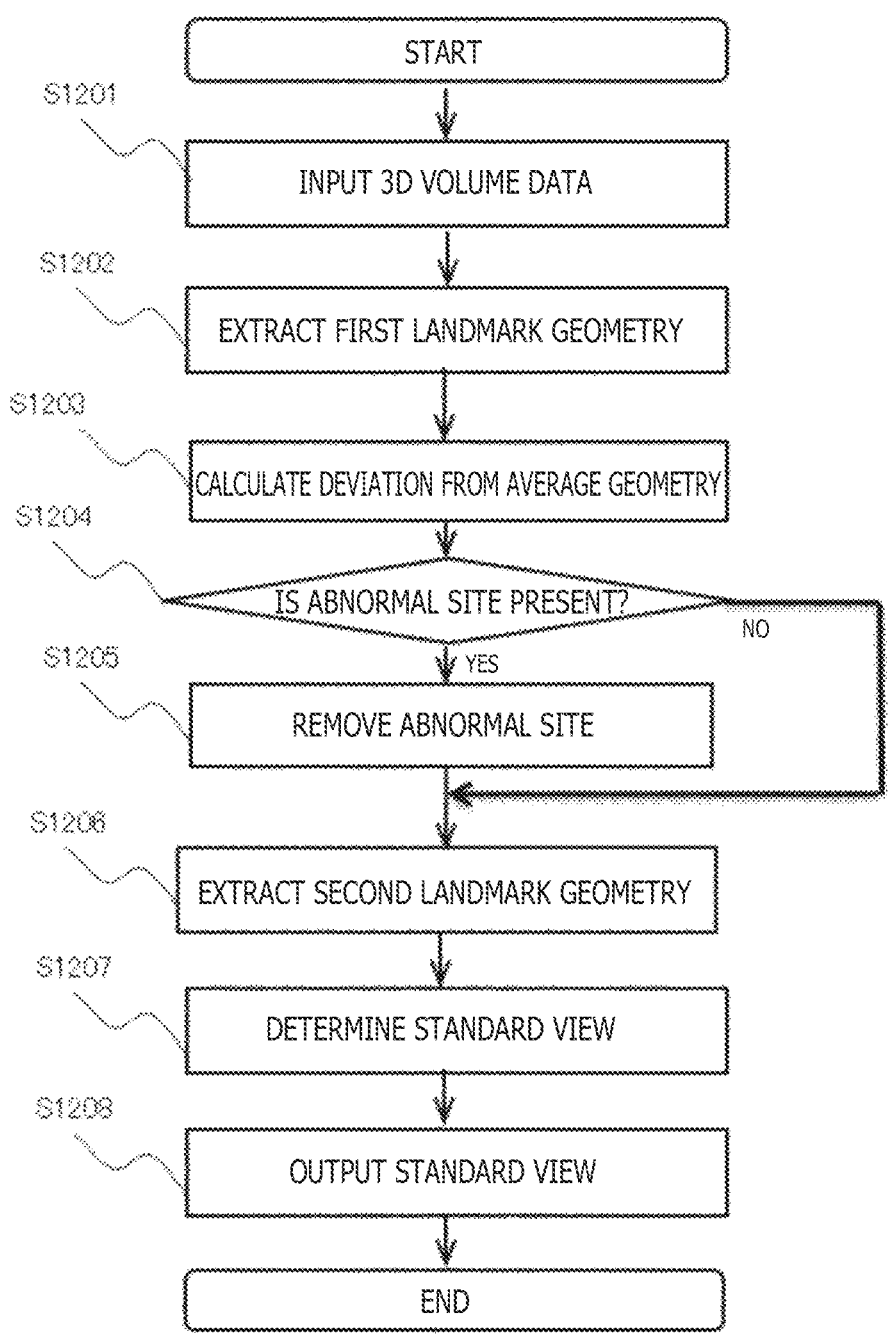
FIG. 12 shows an example of an overall flow of standard view extraction according to the third embodiment.

FIG. 12 shows an example of an overall flow of standard view extraction according to the third embodiment. Like the first and second embodiments, in S1201 to S1202, the image processing apparatus 108 extracts the landmark geometry and extracts a defined landmark geometry. The extracted landmark geometry is referred to as "first landmark geometry" in the present embodiment. In S1203, the image processing apparatus 108 calculates the deviation between the extracted first landmark geometry 1103 and the average geometry 1105 read from the storage device 4. When determining that the deviation is out of the allowable range (YES) in S1204, the image processing apparatus 108 removes the local site as the abnormal site in S1205 and extracts the second landmark geometry in S1206. Next, in S1207, the image processing apparatus 108 determines a standard view on the basis of the second landmark geometry obtained by correction, and outputs the standard view in S1208 to transmit the standard view to the display 16 on which an image of the standard view is displayed like S304 and S1006.

According to the configuration of the present embodiment, the image processing apparatus 108 calculates the deviation between the landmark geometry and the average geometry when the local site is unclear, and removes the local site as the abnormal site when the deviation is out of the allowable range, thereby making it possible to determine and display the standard view only on the basis of the normal landmark geometry. It is, therefore, possible to prevent the user from making false determination based on data containing the abnormal site.

According to the present invention described so far in detail, it is possible to provide the ultrasonic imaging device and the image processing method that can extract the view which satisfies the recommendations in the guideline on the acquisition of the standard views robustly and with high accuracy at a time of using information about the defined landmarks and the defined landmark geometry in the three-dimensional information.

The present invention is not limited to the embodiments described above but encompasses various modifications. For example, the abovementioned embodiments have been described in detail for helping better understanding of the present invention. The present invention is not always limited to the embodiments having all the configurations described so far. Furthermore, the configuration of a certain embodiment can be partially replaced by the configuration of the other embodiment or the configuration of the other embodiment can be added to the configuration of the certain embodiment. Moreover, for a part of the configuration of each embodiment, additions, omissions, and substitutions of the other configurations can be made.

Furthermore, an example in which a program that realizes a part or all of each of the configurations, the functions, the processing units, and the like described above is generated and the CPU executes the program has been described. However, it goes without saying that a part or all thereof may be realized by hardware by, for example, designing a part or all thereof in an integrated circuit. In other words, all or a part of the functions of the image processing apparatus may be realized by, for example, an integrated circuit such as an ASIC (application specific integrated circuit) or an FPGA (field programmable gate array).

DESCRIPTION OF REFERENCE CHARACTERS

1: CPU
2: ROM
3: RAM
4: Storage device
5: Bus
7: Ultrasound probe
11: Medium input unit
12: Storage medium
13: Input control unit
14: Input device
15: Display control unit
16: Display
100: Ultrasonic imaging device
101: Transmission/reception switching unit
102: Transmission unit
105: Receiving unit
106: Control unit
107: Image generation unit
108: Image processing apparatus
120: Subject
121: User interface (UI)
501: Patch model
502: Shape model
503: Landmark geometry
504: Bounding box
901: Geometry
902: Deformed geometry
903: Interface
904: Display region
905: Measured numeric value display region
906: Control bar
907: Manual correction instruction button

The invention claimed is:

1. An ultrasonic imaging device, comprising:
an image processing apparatus configured to:
extract a landmark geometry that contains landmarks in three-dimensional information about a subject obtained by transmitting and receiving ultrasound waves,
determine a standard view based on the three-dimensional information using the landmark geometry and a position relationship that satisfies recommendations in a guideline;
determine the extracted landmark geometry as a first landmark geometry,
calculate a deviation between the first landmark geometry and a stored average geometry of the landmarks,
delete from the first landmark geometry a local geometry, the deviation on the local geometry in the first landmark geometry being equal to or higher than a predetermined value, extract a second landmark geometry that contains the landmark geometries other than the local geometry, and determine the standard view using the extracted second landmark geometry.

2. The ultrasonic imaging device according to claim 1, further comprising an image display unit, wherein the image processing apparatus displays the extracted landmark geometry on the image display unit, and receives a correction instruction to correct the landmark geometry from a user.

3. The ultrasonic imaging device according to claim 2, wherein the image processing apparatus displays a control bar on the image display unit, and deforms the landmark geometry to correspond to the correction instruction by adjustment of the control bar.

4. The ultrasonic imaging device according to claim 2, wherein the image processing apparatus corrects the landmark geometry to correspond to drag-and-drop of a desired site in the landmark geometry displayed in the image display unit.

5. The ultrasonic imaging device according to claim 2, wherein the image processing apparatus displays a length between the landmarks in the image display unit.

6. The ultrasonic imaging device according to claim 2, including a storage unit that stores a relationship between the landmarks and geometric parameters, wherein the image processing apparatus deforms the landmark geometry by adjusting the geometric parameters on the basis of the correction instruction.

7. The ultrasonic imaging device according to claim 1, wherein the image processing apparatus determines a view for which a plurality of position relationships among the landmarks become a maximum in the recommendations as the standard view.

8. The ultrasonic imaging device according to claim 7, wherein the image processing apparatus determines, when there is no view for which the plurality of position relationships become a maximum, a view for which a sum of angles formed between the view and directions of the plurality of position relationships becomes a minimum as the standard view.

9. An image processing method executed by an image processing apparatus, comprising:

extracting a landmark geometry that contains landmarks in three-dimensional information about a subject;

determining a standard view based on the three-dimensional information using the landmark geometry and a position relationship that satisfies recommendations in a guideline;

determining the extracted landmark geometry as a first landmark geometry;

calculating a deviation between the first landmark geometry and an average geometry of the landmarks stored in advance, deleting from the first landmark geometry a local geometry, the deviation on the local geometry in the first landmark geometry being equal to or higher than a predetermined value, and extracting a second landmark geometry that contains landmark other than the local geometry; and determining the standard view using the extracted second landmark geometry.

10. The image processing method according to claim 9, executed by the image processing apparatus, including:

displaying the extracted landmark geometry; and receiving a correction instruction to correct the landmark geometry from a user.

11. The image processing method according to claim 9, executed by the image processing apparatus, including:

storing a relationship between the landmarks and geometric parameters; and deforming the landmark geometry by adjusting the geometric parameters on the basis of the correction instruction.

12. The image processing method according to claim 9, executed by the image processing apparatus, including:

determining a view for which a plurality of position relationships among the landmarks become a maximum in the recommendations as the standard view.

13. The image processing method according to claim 12, executed by the image processing apparatus, including:

determining, when there is no view for which the plurality of position relationships become a maximum, a view for which a sum of angles formed between the view and directions of the plurality of position relationships becomes a minimum as the standard view.

* * * * *